US007501553B2

(12) United States Patent
Chen et al.

(10) Patent No.: US 7,501,553 B2

(45) **Date of Patent: *Mar. 10, 2009**

(54) NON-HUMAN TRANSGENIC MAMMAL COMPRISING A MODIFIED MSP-1 NUCLEIC ACID

(75) Inventors: Li-How Chen, Acton, MA (US); Harry M. Meade, Newton, MA (US)

(73) Assignee: GTC Biotherapeutics, Inc., Framingham, MA (US)

(*) Notice: Subject to any disclaimer, the term of this patent is extended or adjusted under 35 U.S.C. 154(b) by 328 days.

This patent is subject to a terminal disclaimer.

(21) Appl. No.: 10/082,018

(22) Filed: Feb. 20, 2002

(65) Prior Publication Data

US 2002/0144299 A1 Oct. 3, 2002

Related U.S. Application Data

(62) Division of application No. 09/175,684, filed on Oct. 20, 1998, now Pat. No. 6,593,463.

(60) Provisional application No. 60/085,649, filed on May 15, 1998, provisional application No. 60/062,592, filed on Oct. 20, 1997.

(51) Int. Cl.
*C12P 21/00* (2006.01)
*A01K 67/00* (2006.01)

(52) U.S. Cl. .......... 800/14; 800/7

(58) Field of Classification Search .......... 800/4, 800/14, 7, 16, 17, 18

See application file for complete search history.

(56) References Cited

U.S. PATENT DOCUMENTS

| | | | | |
|---|---|---|---|---|
| 4,873,316 A | | 10/1989 | Meade et al. | |
| 5,194,587 A | | 3/1993 | Knapp et al. | |
| 5,225,534 A | | 7/1993 | Certa | |
| 5,231,168 A | * | 7/1993 | Dziegiel et al. | 530/350 |
| 5,304,489 A | | 4/1994 | Rosen | |
| 5,395,614 A | | 3/1995 | Knapp et al. | |
| 5,530,177 A | | 6/1996 | Bleck et al. | |
| 5,543,323 A | | 8/1996 | Ridley et al. | |
| 5,643,578 A | | 7/1997 | Robinson et al. | |
| 5,646,247 A | | 7/1997 | Barnwell et al. | |
| 5,736,131 A | * | 4/1998 | Bosch et al. | 424/93.2 |
| 5,795,737 A | * | 8/1998 | Seed et al. | 435/69.1 |
| 5,856,178 A | | 1/1999 | White et al. | |
| 6,114,148 A | | 9/2000 | Seed et al. | |
| 6,130,062 A | | 10/2000 | Milland et al. | |
| 6,593,463 B1 | | 7/2003 | Chen et al. | |
| 2002/0144299 A1 | | 10/2002 | Chen et al. | |
| 2005/0071890 A1 | | 3/2005 | Chen et al. | |
| 2005/0235371 A1 | | 10/2005 | Chen et al. | |

FOREIGN PATENT DOCUMENTS

| | | |
|---|---|---|
| AU | 199748649 B2 | 4/1998 |
| AU | AU 1997 48649 B2 | 4/1998 |
| AU | 727864 | 1/2001 |
| EP | 0264166 | 4/1988 |
| EP | 0359472 | 3/1990 |
| EP | 0 682 115 A | 11/1995 |
| EP | 0923308 | 11/1997 |
| WO | WO91 08216 A | 6/1991 |
| WO | WO 91/18922 | 12/1991 |
| WO | 94/05796 | 3/1994 |
| WO | WO94 28930 | 12/1994 |
| WO | WO 95/17085 | 6/1995 |
| WO | 96/03051 | 2/1996 |
| WO | 97/26911 | 7/1997 |
| WO | 97/30158 | 8/1997 |
| WO | WO97/30159 | 8/1997 |
| WO | WO 97/30159 | 8/1997 |
| WO | WO97 31115 A | 8/1997 |
| WO | WO98 14583 | 4/1998 |
| WO | WO-99/20766 | 4/1999 |
| WO | WO-99/20774 | 4/1999 |

OTHER PUBLICATIONS

Chattergoon et al, 1997, FASEB J., 11: 753-763.*
Ebert et al, 1991, Biotechnology, 9: 935-838.*
Holder et al, 1985, Nature, 317: 270-273.*
Jongwutiwes et al, 1993, Mol. Biochem. Parasitol., 59: 95-100.*
Ledley et al, 1991, Hum. Gene Ther., 2: 77-83.*
McDonnell et al, 1996, The New England J. Med., 334(1): 42-45.*
Orkin et al, 1995, Report and R commendations of Panel to Assess NIH Investment in Gene Therapy Res.*
Pharmacia Catalogue, 1995, p. 277.*
Wang et al, 1989, J. Biol. Chem., 264(35): 21116-21121.*
Zinkernagel et al, 1993, Fundamental Immunology, 3rd edition, Raven Press.*
Akashi et al, 1994, Blood, 83(11): 3182-3187.*
Velander et al. High-Level Expression of a Heterologous Protein in the Milk of Transgenic Swine Using the cDNA Encoding Human Protein C. Proc. Natl. Acad. Sci. Dec. 1992, vol. 89, pp. 12003-12007.*

(Continued)

*Primary Examiner*—Deborah Crouch
(74) *Attorney, Agent, or Firm*—Wolf, Greenfield & Sacks, P.C.

(57) ABSTRACT

The invention provides modified recombinant nucleic acid sequences (preferably DNA) and methods for increasing the mRNA levels and protein expression of malarial surface protein MSP-1 which is known to be difficult to express in cell culture systems, mammalian cell culture systems, or in transgenic animals. The preferred protein candidates for expression using the recombinant techniques of the invention are MSP-1 proteins expressed from DNA coding sequences comprising reduced overall AT content or AT rich regions and/or mRNA instability motifs and/or rare codons relative to the native MSP-1 gene.

43 Claims, 10 Drawing Sheets

OTHER PUBLICATIONS

Holder et al. Primary Structure of the Precursor to the Three Major Surface Antigens of Plamodium falciparum Merozoites. Nature. Sep. 19, 1985, vol. 317, pp. 270-273.*

Holder et al. Processing of the Precursor to the Major Merozoite Surface Antigens of Plasmodium falciparum. Parasitology. 1987, vol. 94, pp. 199-208.*

Siddiqui et al. Merozoite Surface Coat Precursor Protein Completely Protects Aotus Monkeys Against Plasmodium falciparum Malaria. Proced. Natal. Acad. Sci.. May 1987, vol. 84, pp. 3014-3018.*

Gordon et al.; Genetic Transformation of Mouse Enbryos by Microinjection of Purified DNA; (1980); *Proc. Natl. Acad. Sci.*; 77; pp. 7380-7384.

Gordon et al.; Integration and Stable Germ Line Transmission of Genes Injected into Mouse Pronuclei; (1981); *Science*; 214: pp. 1244-1246.

Brinster et al.; Factors Affecting the Efficiency of Introducing Foreing DNA into Mice by Microinjecting Eggs; (1985); *Proc. Natl. Acad. Sci.*; 82: pp. 4438-4442.

Palmiter et al.; Transgenic Mice; (1985); *Cell*; 41: pp. 343-345.

Wall et al.; Development of Porcine Ova That Were Centrifuged to Permit Visualization of Pronuclei and Nuclei; (1985); *Biol. Reprod.*; 32: pp. 645-651.

Shaw et al.; A Conserved AU Sequence from the 3' Untranslated Region of GM-CSF mRNA Mediates Selective mRNA Degradation; (1986); *Cell*; 46: pp. 659-667.

Simons et al.; Gene Transfer into Sheep; (1998); *Bio/Technology*; 6: pp. 179-183.

Chang et al.; Generalized Immunological Recognition of the Major Merozoite Surface Antigen (gp195) of *Plasmodium falciparum*; (1989); *Proc. Natl. Acad. Sci.*; 86: pp. 6343-6347.

Vilotte et al.; Efficient Tissue-Specific Expression of Bovine α-lactalbumin in Transgenic Mice; (1989); *Eur. J. Biochem.*; 186: pp. 43-48.

Buhler et al.; Rabbit β-Casein Promoter Directs Secretion of Human Interleukin-2 into the Milk of Transgenic Rabbits; (1990); *Bio/Technology*; 8: pp. 140-143.

Ebert et al.; Transgenic Production of A Variant of Human Tissue-Type Plasminogen Activator in Goat Milk Generation of Transgenic Goats . . . ; (1991); *Bio/Technology*; 9: pp. 835-838.

Krimenfort et al.; Generation of Transgenic Dairy Cattle Using 'In Vitro' Embryo Production; (1991) *Bio/Technology*; 9: pp. 844-847.

Wright et al.; High Level Expression of Active Human Alpha-1 Antitrypsin in the Milk of Transgenic Sheep; (1991); *Bio/Technology*, 9: 830-834.

Chang et al.; A Carboxyl-Terminal Fragment of *Plasmodium faliciparum gp 195* Expressed by a Recombinant Baculovirus Induces Antibodies that . . . ; (1992); *J. Immunol*; 149: pp. 548-555.

Soulier et al.; Expression Analysis of Ruminant α-Lactalbumin in Transgenic Mice: Developmental Regulation and General Location of Important *Cis*-Regulatory . . . ; (1992); *FEBS Letters*: 297(1-2): pp. 13-18.

Wall et al.; Making Transgenic Livestock: Genetic Engineering on a Large Scale: (1992); *J. Cell. Biochem.*; 49: pp. 113-120.

Diggs et al.; The Major Merozoite Surface Protein as a Malaria Vaccine Target; (1993); *Parasitology Today*; 9(8): pp. 300-302.

Campbell et al.; Sheep Coloned by Nuclear Transfer from a Cultured Cell Line: (1996); *Nature*; 380: pp. 64-66

Chang et al.; A Recombinant Baculovirus 42-Kilodalton C-Terminal Fragment of *Plasmodium falciparum* Merozoite Surface Protein 1 Protects *Aotus* Monkeys . . . ; (1996); *Infection & Immunity*; 64(1): pp. 253-262.

Hochi et al.; Secretion of Bovine α-Lactalbumin into the Milk of Transgenic Rats, (1992) *Molecular Reprduction and Development* 33:160-164.

Dame et al., Current status of the Plasmodium falciparum genome project. Mol Biochem Parasitol. Jul. 1996;79(1):1-12.

D'Orso et al., TcUBP-1, a developmentally regulated U-rich RNA-binding protein involved in selective mRNA destabilization in trypanosomes. J Biol Chem. Sep. 14, 2001;276(37):34801-9. Epub Jul. 2, 2001.

Gardner et al., DNA vaccines against malaria: immunogenicity and protection in a rodent model. J Pharm Sci. Dec. 1996;85(12): 1294-300.

Graves et al., Comparison of the cost-effectiveness of vaccines and insecticide impregnation of mosquito nets for the prevention of malaria. Ann Trop Med Parasitol. Jun. 1998;92(4):399-410.

Graves et al., Vaccines for preventing malaria. Cochrane Database Syst Rev. 2003;(1):CD000129.

Gutierrez et al., Expression of a bovine kappa-CN cDNA in the mammary gland of transgenic mice utilizing a genomic milk protein gene as an expression cassette. Transgenic Res. Jul. 1996;5(4):271-9.

Jenkins et al., Evolution of base composition and codon usage bias in the genus Flavivirus. J Mol Evol. Apr. 2001;52(4):383-90.

Kalinna et al., DNA vaccines for parasitic infections. Immunol Cell Biol. Aug. 1997;75(4):370-5.

Liebhaber et al., mRNA stability and the control gene expression. Nucleic Acids Symp Ser. 1997;(36):29-32.

Martin et al., Total synthesis and expression in Escherichia coli of a gene encoding human tropoelastin. Gene. Mar. 10, 1995;154(2):159-66.

Nuijens et al., Characterization of recombinant human lactoferrin secreted in milk of transgenic mice. J Biol Chem. Mar. 28, 1997;272(13):8802-7.

Perlak et al., Modification of the coding sequence enhances plant expression of insect control protein genes. Proc Natl Acad Sci USA. Apr. 15, 1991;88(8):3324-8.

Prapunwattana et al., Chemical synthesis of the Plasmodium falciparum dihydrofolate reductase-thymidylate synthase gene. Mol Biochem Parasitol. Dec. 2, 1996;83(1):93-106.

Senior et al., DNA vaccine shows promise for malaria. Mol. Med. Today. Jan. 1999;5(1):2-3.

Shani et al., Expression of human serum albumin in the milk of transgenic mice. Transgenic Res. Sep. 1992;1(5): 195-208.

Urdea et al., Chemical synthesis of a gene for human epidermal growth factor urogastrone and its expression in yeast. Proc Nat Acad Sci USA. Dec. 1983;80(24):7461-5.

Weber et al., Analysis of sequences from the extremely A + T-rich genome of Plasmodium falciparum. Gene. 1987;52(1):103-9.

Wesseling et al., Nucleotide sequence and deduced amino acid sequence of a Plasmodium falciparum actin gene. Mol Biochem Parasitol. Jan. 15, 1988;27(2-3):313-20.

Wu et al., Transfection of Plasmodium falciparum within human red blood cells. Proc Natl Acad Sci USA. Feb. 14, 1995;92(4):973-7.

Zientz et al., Genome interdependence in insect-bacterium symbioses. Genome Biol. 2001;2(12):Reviews1032. Epub Nov. 22, 2001.

Carver et al., Expression of Human Alpha 1 Antitrypsin In Transgenic Sheep. Cytotechnology. 1992;9(1-3):77-84.

Eskridge et al., The NH2 terminus of preproinsulin directs the translocation and glycosylation of a bacterial cytoplasmic protein by mammalian microsomal membranes. J. Cell. Biol. 103(6):2263-2272 (1996).

Hirabayashi et al., Transgene Expression In Mammary Glands of Newborn Rats. Mol. Reprod. Dev. Feb. 1996;43(2):145-9.

Holder et al., The precursor to major merozoite surface antigens: structure and role in immunity. Prog. Allergy. 41:72-97 (1988).

Kotula et al., Evaluation of foreign gene codon optimization in yeast: expression of a mouse IG kappa chain. Biotechnology 9(10):1386-1389.

Marshall et al., Naturally occurring splicing variants of the hMSH2 gene containing nonsense codons identify possible mRNA instability motifs within the gene coding region, Biochimica et Biophysica Acta, Jul. 31, 1996; 1308(1):88-92.

Peterson et al., Variation in the precursor to the major merozoite surface antigens of Plasmodium falciparum. Mol. Biochem. Parisitol 27:291-302 (1988).

Prunkard et al., High-Level Expression o f Recombinant Human Fibrinogen In the Milk of Transgenic Mice. Nat. Biotechnol. Jul. 1996;14(7):867-71.

Reeck et al., Homology in protein and nucleic acids: a terminology muddle and a way out of it. Cell Aug. 28, 1987; 50:667.

Van Cott et al., Affinity Purification of Biologically Active and Inactive Forms of Recombinant Human Protein C Produced In Porcine Mammary Gland. J. Mol. Recognit. Sep.-Dec. 1996; 9(5-6):407-14.

Wang et al., Molecular cloning, gene organization and expression of rainbow trout (*Oncorhynchus mykiss*) inducible nitric oxide synthase (iNOS) gene. J. Biochem. 2001: 358:747-55.

Ziomek Minimization of Viral Contamination in Human Pharmaceuticals Produced in the Milk of Transgenic Goats. Dev. Biol. Stand. 1996;88:265-8.

Myler, Nucleotide and deduced amino acids sequence of the gp195 (MSA-1) gene from Plasmodium falciparum Palo Alto PLF-3/B11. 1989 Nucleic Acids Research 17: 5401.

Romanos et al., Expression of tetanus toxin fragment C in yeast: gene synthesis is required to eliminate fortuitous polyadenylation in AT-rich DNA. 1991 Nucleic Acids Research 19: 1461-1467.

Notice of Allowance and Fees Due with Examiner's Comments and Examiner-Initiated Interview Summary mailed Nov. 19, 2007 for U.S. Appl. No. 11/140,676 (G0744.70031US04, Chen et al., filed May 27, 2005).

Hogh et al., "Antibodies to a recombinant glutamate-rich *Plasmodium Falciparum* protein: evidence for protection of individuals living in a holoendemic area of liberia," *Am. J. Trop. Med. Hyg.*, 1992, 46(3):307-13.

Kocken et al., "High-level expression of *Plasmodium vivax* apical membrane antigen 1 (AMA-1) in *Pichia pastoris*: strong immunogenicity in *Macaca mulatta* immunized with *P. vivax* AMA-1 and Adjuvant SBAS2," *Inf. Imm.*, 1999, 67(1):43-9.

Theisen et al., "Antigenicity and immunogenicity of recombinant glutamate-rich protein of *Plasmodium falciparum* expressed in *Escherichia coli*," *Clin. Diag. Lab. Immunol.*, 1995, 2(1):30-4.

Theisen et al., "The glutamate-rich protein (GLURP) of *Plasmodium falciparum* is a target for antibody-dependent monocyte-mediated inhibition of parasite growth in vitro," *Inf. Imm.*, 1998, 66(1):11-7.

* cited by examiner

```
  1 GCCGTCACTCCCTCCGTCATCGATAACATCCTGTCCAAGATCGAGAAGGAGTACG
 1▶ A l a Va l Thr Pro Ser Va l I l eAspAsn I l eLeuSer Lys I l eG l uAsnG l uTyr G

56 AGGTGCTGTACCTGAAGCCGCTGGCAGGGGTCTACCGGAGCCTGAAGAAGCAG
19▶ l uVa l LeuTyr LeuLys Pro LeuA l aG l yVa l Tyr Ar g Ser LeuLys Lys G l n

109 CTGGAGAACAACGTGATGACCTTCAACGTGAACGTGAAGGATATCCTGAACAGC
37▶ LeuG l uAsnAsnVa l MetTh r PheAsnVa l AsnVa l LysAsp I l eLeuAsn Ser

163 CGGTTCAACAAGCGGGAGAACTTCAAGAACGTGCTGGAGAGCGATCTGATCCC
55▶ A rgPheAsnLys A rgG l uAsn PheLys Asn Va l LeuG l u Ser AspLeu I l e Pr

216 CTACAAGGATCTGACCAGCAGCAACTACGTGGTCAAGGATCCCTACAAGTTCC
72▶ o Tyr Lys AspLeuThr Ser Ser AsnTyr Va l Va l Lys AspProTyr Lys Phe L

269 TGAACAAGGAGAAGAGAGATAAGTTCCTGAGCAGTTACAACTACATCAAGGATAG
90▶ euAsnLys G l uLys A rgAspLys PheLeuSer Ser TyrAsnTyr I l eLysAsp Se

324 CATTGATACCGATATCAACTTCGCCAACGATGTCCTGGGATACTACAAGATCCT
108▶ r I l eAspThr Asp I l eAsn Phe A l aAsnAspVa l LeuG l yTyr Tyr Lys I l e Le

378 GTCCGAGAAGTACAAGAGCGATCTGGATTCAATCAAGAAGTACATCAACGATAA
126▶ uSer G l uLys Tyr Lys Ser AspLeuAspSer I l eLys Lys Tyr I l eAsnAspLy

432 GCAGGGAGAGAACGAGAAGTACCTGCCCTTCCTGAACAACATCGAGACCCTGTA
144▶ s G l nG l yG l uAsnG l uLys Tyr LeuProPhe LeuAsnAsn I l eG l uThr LeuTy

486 CAAGACCGTCAACGATAAGATTGATCTGTTCGTGATCCACCTGGAGGCCAAGGT
162▶ r Lys Th r Va l AsnAspLys I l eAspLeu PheVa l I l eHi s LeuG l uA l aLys Va
                                                              NdeI

540 CCTGAACTACACATATGAGAAGAGCAACGTGGAGGTCAAGATCAAGGAGCTGAA
180▶ l LeuAsnTyr Th r TyrG l uLys Ser AsnVa l G l uVa l Lys I l eLys G l uLeuAs

594 TTACCTGAAGACCATCCAGGATAAGCTGGCCGATTTCAAGAAGAACAACAACTT
198▶ nTyr LeuLys Th r I l eG l nAsp Lys LeuA l aAspPhe Lys Lys Asn Asn Asn Ph

648 CGTCGGGATCGCCGATCTGAGCACCGATTACAACCACAACAACCTGCTGACCAA
216▶ eVa l G l y I l eA l aAspLeu Ser ThrAspTyr AsnHi s AsnAsnLeu LeuThr Ly

702 GTTCCTGAGCACCGGTATGGTCTTCGAAAACCTGGCCAAGACCGTCCTGAGCAA
234▶ s Phe LeuSer Th r G l yMetVa l PheG l uAsnLeuA l aLys Thr Va l LeuSer As

756 CCTGCTGGATGGGAACCTGCAGGGGATGCTGAACATCAGCCAGCACCAGTGTGT
252▶ n LeuLeuAspG l y AsnLeuG l n G l y Met LeuAsn I l e Ser G l nHi s G l n Cys Va

810 GAAGAAGCAGTGTCCCCAGAACAGCGGGTGTTTCAGACACCTGGATGAGAGA
270▶ l LysLys G l nCys Pro G l nAsn Ser G l yCys PheArgHi s LeuAspG l uA rgG l

864 GGAGTGTAAGTGTCTGCTGAACTACAAGCAGGAAGGTGATAAGTGTGTGGAAAAC
288▶ uG l uCys Lys Cys Leu LeuAsnTyr Lys G l nG l y AspLys Cys Va l G l uAsn

919 CCCAATCCTACTTGTAACGAAGAACAATGGTGGATGTGATGCCGATGCCAAGTGTACCG
307▶ ProAsnProTh r CysAsnG l uAsnG l yG l yCysAspA l aAspA l aLys CysTh r G

977 AGGAGGATTCAGGGAGCAACGGGAAGAAGATCACCTGTGAGTGTACCAAGCCTGATT
326▶ l uG l uAspSer G l y Ser AsnG l y Lys Lys I l eTh r CysG l uCysTh r Lys ProAspS

1034 CTTATCCACTGTTCGATGGTATCTTCTGTAGT
345▶ er Tyr ProLeu PheAspG l y I l e PheCys Ser
```

FIG. 1

```
  1 GCAGTAACTCCTTCCGTAATTGATAACATACTTTCTAAAATTGAAAATGAATA
  1▶ AlaValThrProSerValIleAspAsnIleLeuSerLysIleGluAsnGluTyrG
                           EcoNI (73)
 56 AGGTTTTATATTTAAAACCTTTAGCAGGTGTTTATAGAAGTTTAAAAAAACAATT
 19▶ luValLeuTyrLeuLysProLeuAlaGlyValTyrArgSerLeuLysLysGlnLe
111 AGAAAATAACGTTATGACATTTAATGTTAATGTTAAGGATATTTTAAATTCACGA
 37▶ uGluAsnAsnValMetThrPheAsnValAsnValLysAspIleLeuAsnSerArg
166 TTTAATAAACGTGAAAATTTCAAAAATGTTTTAGAATCAGATTTAATTCCATATA
 56▶ PheAsnLysArgGluAsnPheLysAsnValLeuGluSerAspLeuIleProTyrL
221 AAGATTTAACATCAAGTAATTATGTTGTCAAAGATCCATATAAATTTCTTAATAA
 74▶ ysAspLeuThrSerSerAsnTyrValValLysAspProTyrLysPheLeuAsnLy
276 AGAAAAAAGAGATAAATTCTTAAGCAGTTATAATTATATTAAGGATTCAATAGAT
 92▶ sGluLysArgAspLysPheLeuSerSerTyrAsnTyrIleLysAspSerIleAsp
331 ACGGATATAAATTTTGCAAATGATGTTCTTGGATATTATAAAATATTATCCGAAA
111▶ ThrAspIleAsnPheAlaAsnAspValLeuGlyTyrTyrLysIleLeuSerGluL
386 AATATAAATCAGATTTAGATTCAATTAAAAAATATATCAACGACAAACAAGGTGA
129▶ ysTyrLysSerAspLeuAspSerIleLysLysTyrIleAsnAspLysGlnGlyGl
441 AAATGAGAAATACCTTCCCTTTTTAAACAATATTGAGACCTTATATAAAACAGTT
147▶ uAsnGluLysTyrLeuProPheLeuAsnAsnIleGluThrLeuTyrLysThrVal
496 AATGATAAAATTGATTTATTTGTAATTCATTTAGAAGCAAAAGTTCTAAATTATA
166▶ AsnAspLysIleAspLeuPheValIleHisLeuGluAlaLysValLeuAsnTyrT
551 CATATGAGAAATCAAACGTAGAAGTTAAAATAAAAGAACTTAATTACTTAAAAAC
184▶ hrTyrGluLysSerAsnValGluValLysIleLysGluLeuAsnTyrLeuLysTh
606 AATTCAAGACAAATTGGCAGATTTTAAAAAAAATAACAATTTCGTTGGAATTGCT
202▶ rIleGlnAspLysLeuAlaAspPheLysLysAsnAsnAsnPheValGlyIleAla
661 GATTTATCAACAGATTATAACCATAATAACTTATTGACAAAGTTCCTTAGTACAG
221▶ AspLeuSerThrAspTyrAsnHisAsnAsnLeuLeuThrLysPheLeuSerThrG
716 GTATGGTTTTTGAAAATCTTGCTAAAACCGTTTATCTAATTTACTTGATGGAAA
239▶ lyMetValPheGluAsnLeuAlaLysThrValLeuSerAsnLeuLeuAspGlyAs
771 CTTGCAAGGTATGTTAAACATTTCACAACACCAATGCGTAAAAAAACAATGTCCA
257▶ nLeuGlnGlyMetLeuAsnIleSerGlnHisGlnCysValLysLysGlnCysPro
826 CAAAATTCTGGATGTTTCAGACATTTAGATGAAAGAGAAGAATGTAAATGTTTAT
276▶ GlnAsnSerGlyCysPheArgHisLeuAspGluArgGluGluCysLysCysLeuL
881 TAAATTACAAACAAGAAGGTGATAAATGTGTTGAAAATCCAAATCCTACTTGTAA
294▶ euAsnTyrLysGlnGluGlyAspLysCysValGluAsnProAsnProThrCysAs
936 CGAAAATAATGGTGGATGTGATGCAGATGCCAAATGTACCGAAGAAGATTCAGGT
312▶ nGluAsnAsnGlyGlyCysAspAlaAspAlaLysCysThrGluGluAspSerGly
991 AGCAACGGAAAGAAAATCACATGTGAATGTACTAAACCTGATTCTTATCCACTTT
331▶ SerAsnGlyLysLysIleThrCysGluCysThrLysProAspSerTyrProLeuP
                          PstI (1059)
1046 TCGATGGTATTTTCTGCAGTCACCACCACCACCACCACTAACT
349▶ heAspGlyIlePheCysSerHisHisHisHisHisHis•••
```

FIG. 2

| Codon | AA | goat b-casein | goat K-casein | MSP wt | Edited MSP | mouse b-casein | mouse a-casein | mouse g-casein | mouse e-casein |
|---|---|---|---|---|---|---|---|---|---|
| TTT | Phe | 5 | 4 | 8 | 0 | 4 | 8 | 3 | 4 |
| TTC | Phe | 4 | 3 | 7 | 15 | 4 | 6 | 7 | 1 |
| TTA | Leu | 0 | 2 | 25 | 0 | 0 | 0 | 0 | 0 |
| TTG | Leu | 0 | 2 | 3 | 0 | 0 | 0 | 0 | 1 |
| TCT | Ser | 5 | 1 | 4 | 1 | 13 | 5 | 7 | 5 |
| TCC | Ser | 2 | 2 | 2 | 3 | 6 | 14 | 8 | 2 |
| TCA | Ser | 1 | 4 | 10 | 1 | 1 | 3 | 2 | 0 |
| TCG | Ser | 0 | 1 | 0 | 0 | 0 | 0 | 0 | 0 |
| TAT | Tyr | 2 | 7 | 17 | 2 | 1 | 3 | 2 | 1 |
| TAC | Tyr | 1 | 2 | 3 | 18 | 2 | 6 | 6 | 7 |
| TAA | *** | 1 | 2 | 0 | 0 | 1 | 0 | 1 | 0 |
| TAG | *** | 0 | 0 | 0 | 0 | 0 | 0 | 0 | 0 |
| TGT | Cys | 1 | 1 | 10 | 12 | 0 | 0 | 1 | 0 |
| TGC | Cys | 0 | 2 | 2 | 0 | 2 | 2 | 2 | 1 |
| TGA | *** | 0 | 0 | 0 | 0 | 0 | 1 | 0 | 1 |
| TGG | Trp | 1 | 1 | 0 | 0 | 0 | 2 | 2 | 2 |
| CTT | Leu | 9 | 1 | 9 | 0 | 16 | 9 | 3 | 3 |
| CTC | Leu | 5 | 2 | 0 | 0 | 7 | 8 | 0 | 1 |
| CTA | Leu | 1 | 2 | 1 | 0 | 1 | 2 | 1 | 0 |
| CTG | Leu | 11 | 5 | 0 | 38 | 10 | 17 | 4 | 1 |
| CCT | Pro | 17 | 6 | 4 | 2 | 8 | 6 | 3 | 0 |
| CCC | Pro | 12 | 0 | 1 | 6 | 8 | 6 | 6 | 4 |
| CCA | Pro | 3 | 13 | 5 | 1 | 5 | 6 | 2 | 2 |
| CCG | Pro | 1 | 1 | 0 | 1 | 0 | 0 | 0 | 1 |
| CAT | His | 0 | 1 | 3 | 0 | 2 | 6 | 2 | 1 |
| CAC | His | 5 | 3 | 1 | 4 | 4 | 0 | 3 | 0 |
| CAA | Gln | 5 | 9 | 9 | 0 | 9 | 21 | 9 | 7 |
| CAG | Gln | 16 | 6 | 0 | 9 | 21 | 32 | 12 | 8 |
| CGT | Arg | 0 | 1 | 1 | 0 | 0 | 0 | 0 | 0 |
| CGC | Arg | 0 | 0 | 0 | 0 | 1 | 0 | 0 | 0 |
| CGA | Arg | 0 | 0 | 1 | 0 | 0 | 0 | 0 | 1 |
| CGG | Arg | 1 | 0 | 0 | 3 | 0 | 0 | 0 | 0 |
| ATT | Ile | 4 | 5 | 13 | 0 | 3 | 4 | 3 | 4 |
| ATC | Ile | 6 | 3 | 2 | 20 | 7 | 5 | 8 | 5 |
| ATA | Ile | 1 | 3 | 5 | 0 | 1 | 0 | 2 | 0 |
| ATG | Met | 7 | 3 | 3 | 3 | 4 | 12 | 2 | 13 |
| ACT | Thr | 7 | 6 | 3 | 2 | 6 | 5 | 1 | 4 |
| ACC | Thr | 2 | 7 | 3 | 13 | 4 | 4 | 4 | 4 |
| ACA | Thr | 2 | 4 | 9 | 1 | 1 | 1 | 2 | 0 |
| ACG | Thr | 0 | 0 | 1 | 0 | 0 | 0 | 2 | 0 |
| AAT | Asn | 2 | 6 | 29 | 3 | 4 | 6 | 3 | 1 |
| AAC | Asn | 2 | 3 | 12 | 38 | 4 | 9 | 4 | 6 |
| AAA | Lys | 7 | 6 | 38 | 0 | 6 | 7 | 3 | 5 |
| AAG | Lys | 6 | 4 | 4 | 42 | 3 | 6 | 13 | 7 |
| AGT | Ser | 2 | 6 | 5 | 2 | 3 | 6 | 6 | 5 |
| AGC | Ser | 5 | 0 | 2 | 16 | 2 | 6 | 6 | 3 |
| AGA | Arg | 2 | 2 | 4 | 3 | 1 | 8 | 1 | 1 |
| AGG | Arg | 0 | 2 | 0 | 0 | 0 | 0 | 0 | 1 |
| GTT | Val | 5 | 6 | 15 | 0 | 7 | 4 | 2 | 3 |
| GTC | Val | 8 | 2 | 1 | 11 | 7 | 3 | 3 | 0 |
| GTA | Val | 2 | 2 | 5 | 0 | 2 | 4 | 1 | 3 |
| GTG | Val | 8 | 4 | 0 | 10 | 6 | 3 | 5 | 3 |
| GCT | Ala | 1 | 3 | 2 | 0 | 8 | 17 | 4 | 2 |
| GCC | Ala | 4 | 7 | 1 | 8 | 6 | 3 | 3 | 3 |
| GCA | Ala | 3 | 7 | 6 | 1 | 4 | 13 | 1 | 1 |
| GCG | Ala | 0 | 1 | 0 | 0 | 0 | 0 | 0 | 0 |
| GAT | Asp | 4 | 5 | 25 | 27 | 3 | 6 | 4 | 2 |
| GAC | Asp | 0 | 2 | 2 | 0 | 1 | 2 | 1 | 3 |
| GAA | Glu | 10 | 6 | 21 | 3 | 6 | 12 | 9 | 6 |
| GAG | Glu | 9 | 5 | 4 | 22 | 5 | 5 | 5 | 5 |
| GGT | Gly | 2 | 1 | 8 | 4 | 0 | 0 | 0 | 0 |
| GGC | Gly | 0 | 0 | 0 | 0 | 0 | 0 | 0 | 0 |
| GGA | Gly | 2 | 1 | 6 | 3 | 1 | 0 | 1 | 0 |
| GGG | Gly | 1 | 0 | 0 | 7 | 1 | 0 | 0 | 0 |

FIG. 3A

| Codon | AA | MSP wt | Edited MSP | MSP wt | Edited MSP | E.coli | Human |
|---|---|---|---|---|---|---|---|
| TTT | Phe | 8 | 0 | 0.53 | 0 | 0.5 | 0.35 |
| TTC | Phe | 7 | 15 | 0.47 | 1 | 0.5 | 0.65 |
| TTA | Leu | 25 | 0 | 0.66 | 0 | 0.11 | 0.05 |
| TTG | Leu | 3 | 0 | 0.08 | 0 | 0.11 | 0.09 |
| TCT | Ser | 4 | 1 | 0.17 | 0.04 | 0.27 | 0.17 |
| TCC | Ser | 2 | 3 | 0.09 | 0.13 | 0.21 | 0.26 |
| TCA | Ser | 10 | 1 | 0.43 | 0.04 | 0.13 | 0.11 |
| TCG | Ser | 0 | 0 | 0 | 0 | 0.14 | 0.07 |
| TAT | Tyr | 17 | 2 | 0.85 | 0.1 | 0.54 | 0.47 |
| TAC | Tyr | 3 | 18 | 0.15 | 0.9 | 0.46 | 0.53 |
| TAA | *** | 0 | 0 | | | | |
| TAG | *** | 0 | 0 | | | | |
| TGT | Cys | 10 | 12 | 0.83 | 1 | 0.45 | 0.3 |
| TGC | Cys | 2 | 0 | 0.17 | 0 | 0.55 | 0.7 |
| TGA | *** | 0 | 0 | | | | |
| TGG | Trp | 0 | 0 | 0 | 0 | 1 | 1 |
| CTT | Leu | 9 | 0 | 0.24 | 0 | 0.12 | 0.11 |
| CTC | Leu | 0 | 0 | 0 | 0 | 0.12 | 0.22 |
| CTA | Leu | 1 | 0 | 0.02 | 0 | 0.03 | 0.07 |
| CTG | Leu | 0 | 38 | 0 | 1 | 0.72 | 0.46 |
| CCT | Pro | 4 | 2 | 0.4 | 0.2 | 0.14 | 0.24 |
| CCC | Pro | 1 | 6 | 0.1 | 0.6 | 0.11 | 0.41 |
| CCA | Pro | 5 | 1 | 0.5 | 0.1 | 0.2 | 0.24 |
| CCG | Pro | 0 | 1 | 0 | 0.1 | 0.54 | 0.11 |
| CAT | His | 3 | 0 | 0.75 | 0 | 0.64 | 0.42 |
| CAC | His | 1 | 4 | 0.25 | 1 | 0.36 | 0.58 |
| CAA | Gln | 9 | 0 | 1 | 0 | 0.31 | 0.26 |
| CAG | Gln | 0 | 9 | 0 | 1 | 0.69 | 0.74 |
| CGT | Arg | 1 | 0 | 0.17 | 0 | 0.46 | 0.09 |
| CGC | Arg | 0 | 0 | 0 | 0 | 0.32 | 0.19 |
| CGA | Arg | 1 | 0 | 0.17 | 0 | 0.05 | 0.1 |
| CGG | Arg | 0 | 3 | 0 | 0.5 | 0.06 | 0.15 |
| ATT | Ile | 13 | 0 | 0.65 | 0 | 0.39 | 0.23 |
| ATC | Ile | 2 | 20 | 0.1 | 1 | 0.52 | 0.64 |
| ATA | Ile | 5 | 0 | 0.25 | 0 | 0.08 | 0.13 |
| ATG | Met | 3 | 3 | 1 | 1 | 1 | 1 |
| ACT | Thr | 3 | 2 | 0.19 | 0.13 | 0.36 | 0.2 |
| ACC | Thr | 3 | 13 | 0.19 | 0.81 | 0.38 | 0.47 |
| ACA | Thr | 9 | 1 | 0.56 | 0.06 | 0.09 | 0.21 |
| ACG | Thr | 1 | 0 | 0.06 | 0 | 0.17 | 0.12 |
| AAT | Asn | 29 | 3 | 0.71 | 0.07 | 0.29 | 0.34 |
| AAC | Asn | 12 | 38 | 0.29 | 0.93 | 0.71 | 0.66 |
| AAA | Lys | 38 | 0 | 0.9 | 0 | 0.72 | 0.45 |
| AAG | Lys | 4 | 42 | 0.1 | 1 | 0.28 | 0.55 |
| AGT | Ser | 5 | 2 | 0.21 | 0.09 | 0.11 | 0.11 |
| AGC | Ser | 2 | 16 | 0.09 | 0.7 | 0.14 | 0.29 |
| AGA | Arg | 4 | 3 | 0.67 | 0.5 | 0.08 | 0.24 |
| AGG | Arg | 0 | 0 | 0 | 0 | 0.03 | 0.23 |
| GTT | Val | 15 | 0 | 0.71 | 0 | 0.37 | 0.13 |
| GTC | Val | 1 | 11 | 0.05 | 0.52 | 0.12 | 0.27 |
| GTA | Val | 5 | 0 | 0.24 | 0 | 0.28 | 0.09 |
| GTG | Val | 0 | 10 | 0 | 0.48 | 0.23 | 0.5 |
| GCT | Ala | 2 | 0 | 0.22 | 0 | 0.33 | 0.31 |
| GCC | Ala | 1 | 8 | 0.11 | 0.89 | 0.18 | 0.4 |
| GCA | Ala | 6 | 1 | 0.67 | 0.11 | 0.28 | 0.17 |
| GCG | Ala | 0 | 0 | 0 | 0 | 0.21 | 0.12 |
| GAT | Asp | 25 | 27 | 0.93 | 1 | 0.48 | 0.38 |
| GAC | Asp | 2 | 0 | 0.07 | 0 | 0.52 | 0.62 |
| GAA | Glu | 21 | 3 | 0.84 | 0.12 | 0.67 | 0.4 |
| GAG | Glu | 4 | 22 | 0.16 | 0.88 | 0.33 | 0.6 |
| GGT | Gly | 8 | 4 | 0.57 | 0.29 | 0.46 | 0.15 |
| GGC | Gly | 0 | 0 | 0 | 0 | 0.4 | 0.44 |
| GGA | Gly | 6 | 3 | 0.43 | 0.21 | 0.06 | 0.17 |
| GGG | Gly | 0 | 7 | 0 | 0.5 | 0.08 | 0.24 |

FIG. 3B

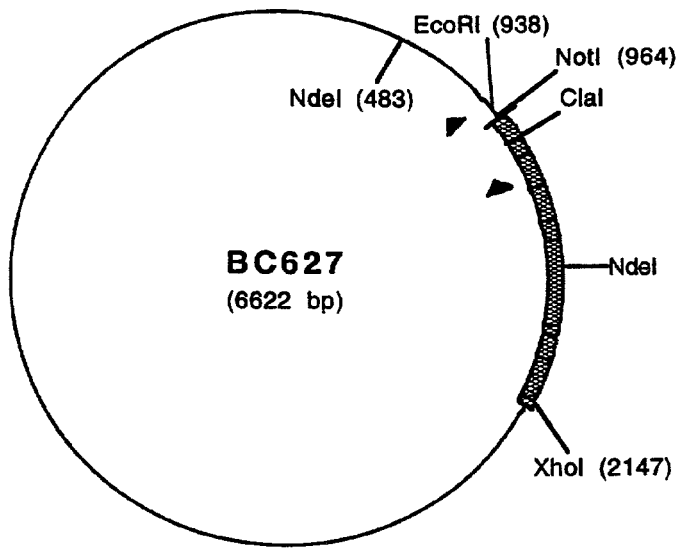

FIG. 4C

Oligos used:

OT1:
TCG ACG AGA GCC ATG AAG GTC CTC ATC CTT GCC TGT CTG GTG GCT CTG GCC ATT GCA AGA GAG CAG GAA GAA CTC AAT GTA GTC GGT A,

OT2:
GAT CTA CCG ACT ACA TTG AGT TCT TCC TGC TCT CTT GCA ATG GCC AGA GCC ACC AGA CAG GCA AGG ATG AGG ACC TTC ATG GCT CTC G,

MSP1:
AATAGATCTGCAGTAACTCCTTCCGTAATTG,

MSP2:
AATTCTCGAGTTAGTGGTGGTGGTGGTGGTGACTGCAGAAATACCATC

MSP8:
TAACTCGAGCGAACCATGAAGGTCCTCATCCTTGCCTGTCTGGTGGCTCTGG
CCATTGCA

FIG. 6

PANEL A     PANEL B

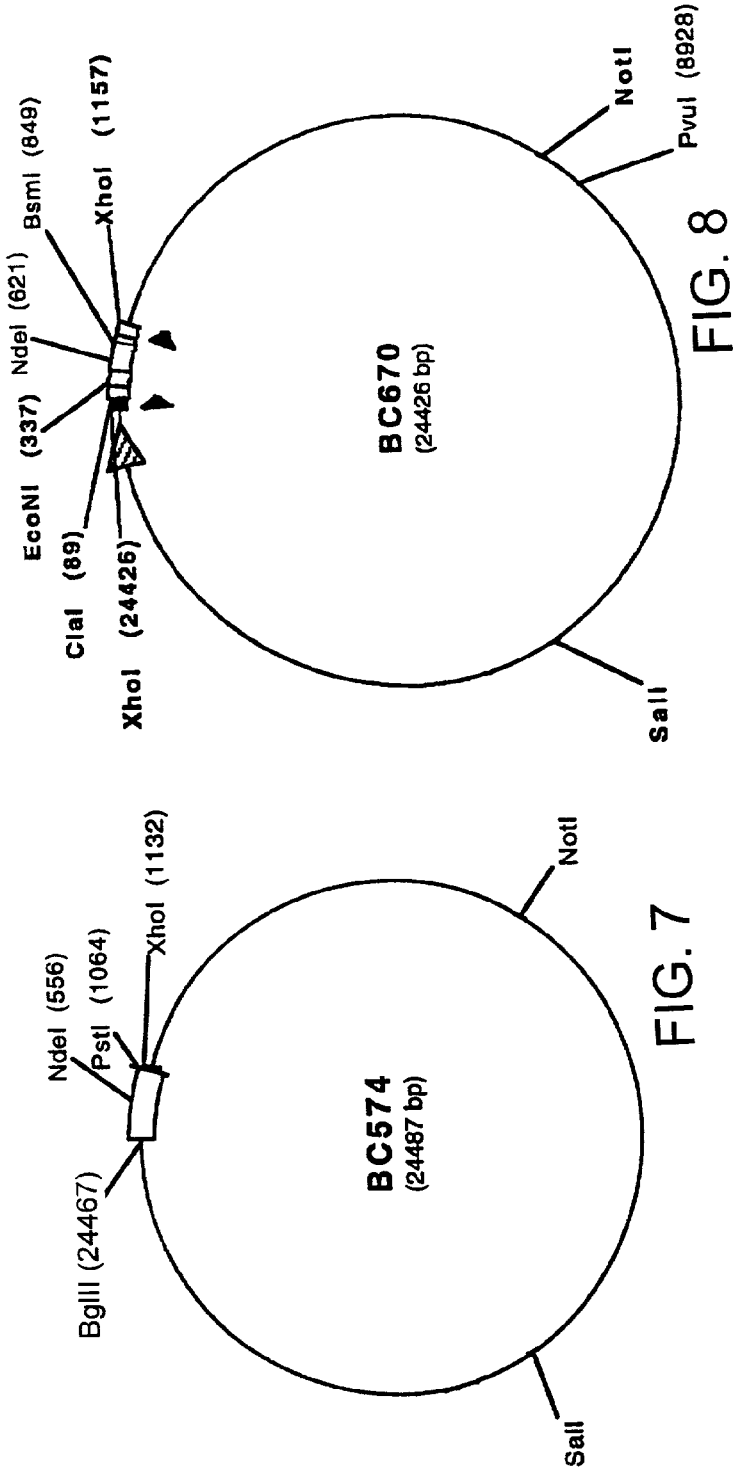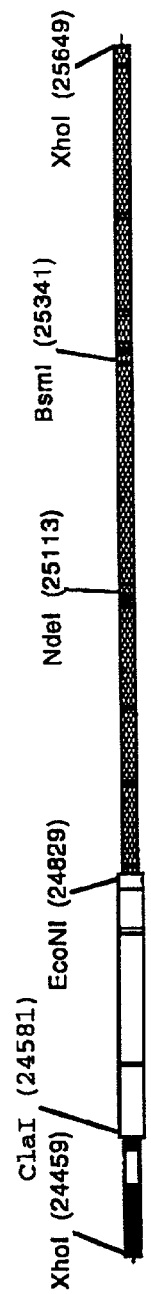

```
 26 ATGAAGGTCCTCATAATTGCCTGTCTGGTGGCTCTGGCCATTGCAGCCGTCACTCCCTCCGTCATCGATAAC

1▶ M  K  V  L  I  I  A  C  L  V  A  L  A  I  A  A  V  T  P  S  V  I  D  N
 98 ATCCTGTCCAAGATCGAGAACGAGTACGAGGTGCTGTACCTGAAGCCCCTGGCAGGAGTCTACAGGAGCCT

25▶ I  L  S  K  I  E  N  E  Y  E  V  L  Y  L  K  P  L  A  G  V  Y  R  S  L
169 GAAGAAGCAGCTGGAGAACAACGTGATGACCTTCAACGTGAACGTGAAGGATATCCTGAACAGCAGGTTCAA

48▶ K  K  Q  L  E  N  N  V  M  T  F  N  V  N  V  K  D  I  L  N  S  R  F  N
241 CAAGAGGGAGAACTTCAAGAACGTGCTGGAGAGCGATCTGATCCCCTACAAGGATCTGACCAGCAGCAACTA

72▶ K  R  E  N  F  K  N  V  L  E  S  D  L  I  P  Y  K  D  L  T  S  S  N  Y
                                    EcoNI (337)
313 CGTGGTCAAAGATCCCTACAAGTTCCTGAACAAGGAGAAGAGAGATAAGTTCCTGAGCAGTTACAATTACAT
                                          ──────▶

96▶ V  V  K  D  P  Y  K  F  L  N  K  E  K  R  D  K  F  L  S  S  Y  N  Y  I
385 CAAGGATAGCATTGACACCGATATCAACTTCGCCAACGATGTCCTGGGATACTACAAGATCCTGTCCGAGAA

120▶ K  D  S  I  D  T  D  I  N  F  A  N  D  V  L  G  Y  Y  K  I  L  S  E  K
457 GTACAAGAGCGATCTGGATAGCATCAAGAAGTACATCAACGATAAGCAGGGAGAGAACGAGAAGTACCTGCC

144▶ Y  K  S  D  L  D  S  I  K  K  Y  I  N  D  K  Q  G  E  N  E  K  Y  L  P
529 CTTCCTGAACAACATCGAGACCCTGTACAAGACCGTCAACGATAAGATTGATCTGTTCGTGATCCACCTGGA

168▶ F  L  N  N  I  E  T  L  Y  K  T  V  N  D  K  I  D  L  F  V  I  H  L  E
                       NdeI (621)
601 GGCCAAGGTCCTGCAGTACACATATGAGAAGAGCAACGTGGAGGTCAAGATCAAGGAGCTGAATTACCTGAA
                              ◀──────

192▶ A  K  V  L  Q  Y  T  Y  E  K  S  N  V  E  V  K  I  K  E  L  N  Y  L  K
673 GACCATCCAGGATAAGCTGGCCGATTTCAAGAAGAACAACAACTTCGTCGGAATCGCCGATCTGAGCACCGA

216▶ T  I  Q  D  K  L  A  D  F  K  K  N  N  N  F  V  G  I  A  D  L  S  T  D
745 TTACAACCACAACAACCTGCTGACCAAGTTCCTGAGCACCGGAATGGTCTTCGAAAACCTGGCCAAGACCGT

240▶ Y  N  H  N  N  L  L  T  K  F  L  S  T  G  M  V  F  E  N  L  A  K  T  V
                                  BsmI (849)
817 CCTGAGCAACCTGCTGGATGGAAACCTGCAGGGAATGCTGCAGATCAGCCAGCACCAGTGTGTGAAGAAGC
                                         ──────▶

264▶ L  S  N  L  L  D  G  N  L  Q  G  M  L  Q  I  S  Q  H  Q  C  V  K  K
888 AGTGTCCCCAGAACAGCGGATGCTTCAGACACCTGGATGAGAGGGAGGAGTGCAAGTGCCTGCTGAACTA

288▶ Q  C  P  Q  N  S  G  C  F  R  H  L  D  E  R  E  E  C  K  C  L  L  N  Y
958 CAAGCAGGAAGGAGATAAGTGTGTGGAAAACCCCAATCCTACTTGTAACGAGAACAATGGAGGATGCGATG

311▶ K  Q  E  G  D  K  C  V  E  N  P  N  P  T  C  N  E  N  N  G  G  C  D
1029 CCGATGCCAAGTGTACCGAGGAGGATTCAGGAAGCAACGGAAAGAAGATCACCTGCGAGTGTACCAAGCCT

335▶ A  D  K  C  T  E  E  D  S  G  S  N  G  K  K  I  T  C  E  C  T  K  P
                                                              XhoI (1157)
1100 GATTCTTATCCACTGTTCGATGGtATtTTCTGCAGTCACCACCACCACCACCACTAACTCGAGGAT
                                                     ◀──────

NON-HUMAN TRANSGENIC MAMMAL COMPRISING A MODIFIED MSP-1 NUCLEIC ACID

CROSS-REFERENCE TO RELATED APPLICATIONS

This application is a division of U.S. Ser. No. 09/175,684, filed Oct. 20, 1998, now U.S. Pat. No. 6,593,463 which claims priority to U.S. Ser. No. 60/085,649, filed May 15, 1998, and U.S. Ser. No. 60/062,592, filed Oct. 20, 1997, the contents of which are incorporated herein by reference.

BACKGROUND OF THE INVENTION

1. Field of the Invention

The invention relates to heterologous gene expression. More particularly, the invention relates to the expression of malaria genes in higher eukaryote cell systems.

2. Summary of the Related Art

Recombinant production of certain heterologous gene products is often difficult in in vitro cell culture systems or in vivo recombinant production systems. For example, many researchers have, found it difficult to express proteins derived from bacteria, parasites and virus in cell culture systems different from the cell from which the protein was originally derived, and particularly in mammalian cell culture systems. One example of a therapeutically important protein which has been difficult to produce by mammalian cells is the malaria merozoite surface protein (MSP-1).

Malaria is a serious heath problem in tropical countries. Resistance to existing drugs is fast developing and a vaccine is urgently needed. Of the number of antigens that get expressed during the life cycle of $P.\ falciparum$, MSP-1 is the most extensively studied and promises to be the most successful candidate for vaccination. Individuals exposed to $P.\ falciparum$ develop antibodies against MSP-1, and studies have shown that there is a correlation between a naturally acquired immune response to MSP-1 and reduced malaria morbidity. In a number of studies, immunization with purified native MSP-1 or recombinant fragments of the protein has induced at least partial protection from the parasite (Diggs et al, (1993) $Parasitol\ Today$ 9:300–3021 Thus MSP-1 is an important target for the development of a vaccine against $P.\ falciparum$.

MSP-1 is a 190–220 kDA glycoprotein. The C-terminal region has been the focus of recombinant production for use as a vaccine. However, a major problem in developing MSP-1 as a vaccine is the difficulty in obtaining recombinant proteins in bacterial or yeast expression systems that are equivalent in immunological potency to the affinity purified native protein (Chang et al., (1992) $J.\ Immunol.$ 148:548–555.) and in large enough quantities to make vaccine production feasible.

Improved procedures for enhancing expression of sufficient quantities of MSP-1 would be advantageous.

BRIEF SUMMARY OF THE INVENTION

The present invention provides improved recombinant DNA compositions and procedures for increasing the mRNA levels and protein expression of the malarial surface antigen MSP-1 in cell culture systems, mammalian cell culture systems, or in transgenic mammals. The preferred protein candidate for expression in an expression system in accordance with the invention is a C-terminal derivative of MSP-1 having a DNA coding sequence with reduced AT content, and eliminated mRNA instability motifs and rare codons relative to the recombinant expression systems. Thus, in a first aspect, the invention provides a DNA sequence derived from the sequence shown in SEQ ID NO 2. This derivative sequence is shown in SEQ ID NO 1.

In a second aspect, the invention provides a process for preparing a modified nucleic acid of the invention comprising the steps of lowering the overall AT content of the natural gene encoding MSP-1, eliminating all mRNA instability motifs and replacing all rare codons with a preferred codon of the mammary gland tissue, all by replacing specific codons in the natural gene with codons recognizable to, and preferably preferred by mammary gland tissue and which code for the same amino acids as the replaced codon. This aspect of the invention further includes modified nucleic acids prepared according to the process of the invention.

In a third aspect, the invention also provides vectors comprising modified MSP-1 nucleic acids of the invention and a goat beta casein promoter and signal sequence, and host cells transformed with nucleic acids of the invention.

In a fourth aspect, the invention provides transgenic non-human mammals whose germlines comprise a nucleic acid of the invention.

In a fifth aspect, the invention provides a DNA vaccine comprising a modified MSP-1 gene according to the invention.

DESCRIPTION OF THE DRAWINGS

FIG. 1 depicts the cDNA sequence of MSP-$1_{42}$ modified in accordance with the invention [SEQ ID NO 1] in which 306 nucleotide positions have been replaced to lower AT content and eliminate mRNA instability motifs white maintaining the same protein amino acid sequence of MSP-$1_{42}$. The large letters indicate nucleotide substitutions.

FIG. 2 depicts the nucleotide sequence coding sequence of the "wild type" or native MSP-$1_{42}$ [SEQ ID NO 2].

FIG. 3 is a codon usage table for wild type MSP-$1_{42}$ (designated "MSP wt" in the table) and the new modified MSP-$1_{42}$ gene (designated "edited MSP" in the table) and several milk protein genes (casein genes derived from goats and mouse). The numbers in each column indicate the actual number of times a specific codon appears in each of the listed genes. The new MSP-$1_{42}$ synthetic gene was derived from the mammary specific codon usage by first choosing GC rich codons for a given amino acid combined with selecting the amino acids used most frequently in the milk proteins.

FIG. 4a–c depict MSP-$1_{42}$ constructs GTC 479, GTC 564, and GTC 627, respectively as are described in the examples.

FIG. 5 panel B is a Western analysis wherein the eluted fractions after affinity purifications numbers are collected fractions. The results show that fractions from GTC679 the modified MSP-$1_{42}$ synthetic gene construct reacted with polyclonal antibodies to MSP-1 and the negative control GTC479 did not.

FIG. 6 depicts the nucleic acid sequences of OT1 [SEQ ID NO 3], OT2 [SEQ ID NO 4], MSP-8 [SEQ ID ON 5], MSP-2 [SEQ ID NO 6] and MSP1 [SEQ ID NO 7] described in the Examples.

FIG. 7 is a schematic representation of plasmid BC574.

FIG. 8 is a schematic representation of BC620.

FIG. 9 is a schematic representation of BC670.

FIG. 11 is a schematic representation of the nucleotide sequence of MSP42-2 [SEQ ID NO 8].

DETAILED DESCRIPTION OF THE PREFERRED EMBODIMENTS

Figure 4A:
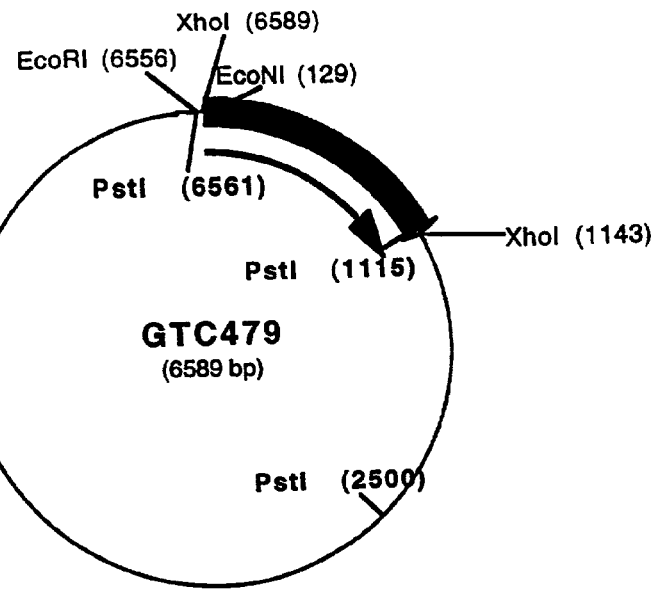

The patent and scientific literature referred to herein establishes the knowledge that is available to those with skill in the art. The issued U.S. patents, allowed applications, published foreign applications, and references cited herein are hereby incorporated by reference. Any conflicts between these references and the present disclosure shall be resolved in favor of the present disclosure.

The present invention provides improved recombinant DNA compositions and procedures for increasing the mRNA levels and protein expression of the malarial surface antigen MSP-1 in cell culture systems, mammalian cell culture systems, or in transgenic mammals. The preferred protein candidate for expression in an expression system in accordance with the invention is a C-terminal derivative of MSP-1 having a DNA coding sequence with reduced AT content, and eliminated mRNA instability motifs and rare codons relative to the recombinant expression systems. Thus, in a first aspect, the invention provides a DNA sequence derived from the sequence shown in SEQ ID NO 2. This derivative sequence is shown in SEQ ID NO 1.

In preferred embodiments, the nucleic acid of the invention is capable of expressing MSP-1 in mammalian cell culture systems, or in transgenic mammals at a level which is at least 25%, and preferably 50% and even more preferably at least 100% or more of that expressed by the natural gene in mammalian cell culture systems, or in transgenic mammals under identical conditions.

As used herein, the term "expression" is meant mRNA transcription resulting in protein expression. Expression may be measured by a number of techniques known in the art including using an antibody specific for the protein of interest. By "natural gene" or "native gene" is meant the gene sequence, or fragments thereof (including naturally occurring allelic variations), which encode the wild type form of MSP-1 and from which the modified nucleic acid is derived A "preferred codon" means a codon which is used more prevalently by the cell or tissue type in which the modified MSP-1 gene is to be expressed, for example, in mammary tissue. Not all codon changes described herein are changes to a preferred codon, so long as the codon replacement is a codon which is at least recognized by the mouse mammary tissue. The term "reduced AT content" as used herein means having a lower overall percentage of nucleotides having A (adenine) or T (thymine) bases relative to the natural MSP-1 gene due to replacement of the A or T containing nucleotide positions or A and/or T containing codons with nucleotides or codons recognized by mouse mammary tissue and which do not change the amino acid sequence of the target protein.

In a second aspect, the invention provides a process for preparing a modified nucleic acid of the invention comprising the steps of lowering the overall AT content of the natural gene encoding MSP-1, eliminating all mRNA instability motifs and replacing all rare codons with a preferred codon of mammary gland tissue, all by replacing specific codons in the natural gene with codons recognizable to, and preferably preferred by mammary gland tissue and which code for the same amino acids as the replaced codon. Standard reference works describing the general principals of recombinant DNA technology include Watson, J. D. et al, *Molecular Biology of the Gene,* Volumes I and II the Benjamin/Cummings Publishing Company, Inc. publisher, Menlo Park, Calif. (1987) Darnell, J. E. et al., *Molecular Cell Biology,* Scientific American Books, Inc., Publisher, New York, N.Y. (1986); Old, R. W., et al., *Principles of Gene Manipulation: An Introduction to Genetic Engineering,* 2d edition, University of California Press, publisher, Berkeley Calif. (1981); Maniatis, T., et al., *Molecular Cloning: A Laboratory Manual,* 2$^{nd}$ ed. Cold Spring Harbor Laboratory, publisher, Cold Spring Harbor, N.Y. (1989) and *Current Protocols in Molecular Biology,* Ausubel et al., Wiley Press, New York, N.Y. (1992). This aspect of the invention further includes modified nucleic acids prepared according to the process of the invention.

Without being limited to any theory, previous research has indicated that a conserved AU sequence (AUUUA) from the 3' untranslated region of GM-CSF mRNA mediates selective mRNA degradation (Shaw, G. and Kamen, R. *Cell* 46:659-667). The focus in the past has been on the presence of these instability motifs in the untranslated region of a gene. The instant invention is the first to recognize an advantage to eliminating the instability sequences in the coding region of the MSP-1 gene.

In a third aspect, the invention also provides vectors comprising modified MSP-1 nucleic acids of the invention and a goat beta casein promoter and signal sequence, and host cells transformed with nucleic acids of the invention.

In a fourth aspect, the invention provides transgenic non-human mammals whose germlines comprise a nucleic acid of the invention. General principals for producing transgenic animals are known in the art. See for example Hogan et al., *Manipulating the Mouse Embryo: A Laboratory Manual,* Cold Spring Harbor Laboratory, (1986); Simons et al, *Bio/Technology* 6:179-183, (1988); Wall et al., *Biol. Reprod.* 32:645-651, (1985); Buhler et al., *Bio/Technology,* 8:140-143 (1990); Ebert et al., *Bio/Technology* 9:835-838 (1991); Krimenfort et at., *Bio/Technology* 9:844-847 (1991); Wall et al., *J. Cell. Biochem.* 49:113-120 (1992). Techniques for introducing foreign DNA sequences into mammals and their germ cells were originally developed in the mouse. See e.g., Gordon et al., *Proc. Natl. Acad. Sci. USA* 77:7380-7384, (1980); Gordon and Ruddle, *Science* 214: 1244-1246 (1981); Palmiter and Brinster, *Cell* 41: 343-345, 1985; Brinster et al., *Proc Natl. Acad Sci., USA* 82:4438-4442 (1985) and Hogan et al. (ibid.). These techniques were subsequently adapted for use with larger animals including cows and goats. Up until very recently, the most widely used procedure for the generation of transgenic mice or livestock, several hundred linear molecules of the DNA of interest in the form of a transgenic expression construct are injected into one of the pro-nuclei of a fertilized egg. Injection of DNA into the cytoplasm of a zygote is also widely used. Most recently cloning of an entire transgenic cell line capable of injection into an unfertilized egg has been achieved (KHS Campbell et al., *Nature* 380 64-66, (1996)).

The mammary gland expression system has the advantages of high expression levels, low cost, correct processing and accessibility. Known proteins, such as bovine and human alpha-lactalbumin have been produced in lactating transgenic animals by several researchers. (Wright et al, *Bio/Technology* 9:830-834 (1991); Vilotte et al, *Eur. J. Biochem.,* 186:43-48 (1989); Hochi et at., *Mol Reprod. And Devel.* 33:160-164 (1992); Soulier et al., *FEBS Letters* 297(1,2):13-18 (1992)) and the system has been shown to produce high levels of protein.

In a fifth aspect, the invention provides a DNA vaccine comprising a modified MSP-1 gene according to the invention. Such DNA vaccines may be delivered without encapsulation, or they may be delivered as part of a liposome, or as part of a viral genome. Generally, such vaccines are delivered in an amount sufficient to allow expression of the modified MSP-1 gene and to elicit an antibody response in an animal, including a human, which receives the DNA vaccine. Subsequent deliveries, at least one week after the first delivery, may be used to enhance the antibody response. Preferred delivery routes include introduction via mucosal membranes, as well as parenteral administration.

EXAMPLES

Creation of Novel Modified MSP-$1_{42}$ Gene

A novel modified nucleic acid encoding the C-terminal fragment of MSP-1 is provided. The novel, modified nucleic acid of the invention encoding a 42 kD C-terminal part of MSP-1 (MSP-$1_{42}$) capable of expression in mammalian cells of the invention is shown in FIG. 1. The natural MSP-$1_{42}$ gene (FIG. 2) was not capable of being expressed in mammalian cell culture or in transgenic mice. Analysis of the natural MSP-$1_{42}$ gene suggested several characteristics that distinguish it from mammalian genes. First, it has a very high overall AT content of 76%. Second, the mRNA instability motif, AUUUA, occurred 10 times in this 1100 bp DNA segment (FIG. 2). To address these differences a new MSP-$1_{42}$ gene was designed. Silent nucleotide substitution was introduced into the native MSP-$1_{42}$ gene at 306 positions to reduce the overall AT content to 49.7%. Each of the 10 AUUUA mRNA instability motifs in the natural gene were eliminated by changes in codon usage as well. To change the codon usage, a mammary tissue specific codon usage table, FIG. 3a, was created by using several mouse and goat mammary specific proteins. The table was used to guide the choice of codon usage for the modified MSP-$1_{42}$ gene as described above. For example as shown in the Table in FIG. 3a, in the natural gene, 65% (25/38) of the Leu was encoded by TTA, a rare codon in the mammary gland. In the modified MSP-$1_{42}$ gene, 100% of the Leu was encoded by CTG, a preferred codon for Leu in the mammary gland.

An expression vector was created using the modified MSP-$1_{42}$ gene by fusing the first 26 amino acids of goat beta-casein to the N-terminal of the modified MSP-$1_{42}$ gene and a SalI-Xho I fragment which carries the fusion gene was subcloned into the XhoI site of the expression vector pCDNA3. A His6 tag was fused to the 3' end of the MSP-$1_{42}$ gene to allow the gene product to be affinity purified. This resulted in plasmid GTC627 (FIG. 4c).

To compare the natural MSP-$1_{42}$ gene construct to the modified MSP-$1_{42}$ nucleic acid of the invention, an expression vector was also created for the natural MSP-$1_{42}$ gene and the gene was added to mammalian cell culture and injected into mice to form transgenic mice as follows:

Construction of the Native MSP-$1_{42}$ Expression Vector

To secrete the truncated merozoite surface protein-1 (MSP-1) of Plasmodium falciparum, the wild type gene encoding the 42KD C-terminal part of MSP-1 (MSP-$1_{42}$) was fused to either the DNA sequence that encodes the first 15 or the first 26 amino acids of the goat beta-casein. This is achieved by first PCR amplify the MSP-1 plasmid (received from Dr. David Kaslow, NIH) with primers MSP1 and MSP2 (FIG. 6), then cloned the PCR product into the TA vector (Invitrogen).

Figure 4B:
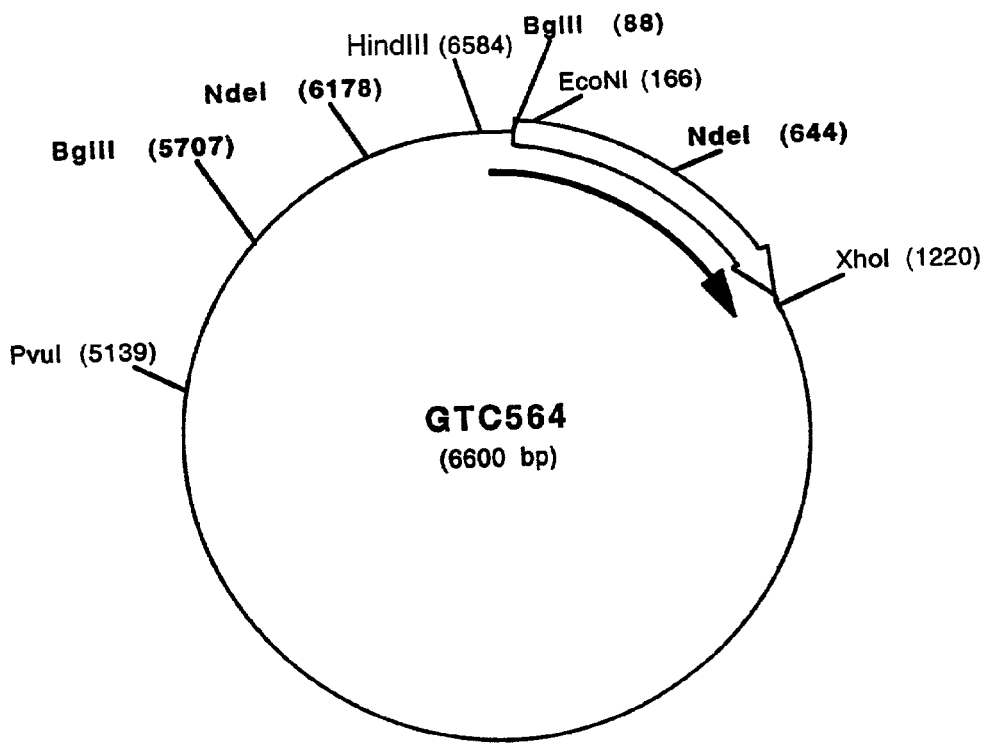

The Bg1II-XhoI fragments of the PCR product was ligated with oligos OT1 and OT2 (FIG. 6) into the expression vector pCDNA3. This yielded plasmid GTC564 (FIG. 4b), which encodes the 15 amino acid beta-casein signal peptide and the first 11 amino acids of the mature goat beta-casein followed by the native MSP-$1_{42}$ gene. Oligos MSP-8 and MSP-2 (FIG. 6) were used to amplify MSP-1 plasmid by PCR, the product was then cloned into TA vector. The XhoI fragment was exercised and cloned into the XhoI site of the expression vector pCDNA3 to yield plasmid GTC479 (FIG. 4a), which encoded 15 amino acid goat beta-casein signal peptide fused to the wild-type MSP-$1_{42}$ gene. A His6 tag was added to the 3' end of MSP-$1_{42}$ gene in GTC 564 and GTC 479.

Native MSP-$1_{42}$ Gene is not Expressed in COS-7 Cells

Expression of the native MSP gene in cultured COS-7 cells was assayed by transient transfection assays. GTC479 and GTC564 plasmids DNA were introduced into COS-7 cells by lipofectamine (Gibco-BRL) according to manufacturer's protocols. Total cellular RNA was isolated from the COS cells two days post-transfection. The newly synthesized proteins were metabolically labeled for 10 hours by adding $^{35}$S methionine added to the culture media two days-post transfection.

To determine the MSP mRNA expression in the COS cells, a Northern blot was probed with a $^{32}$P labeled DNA fragment from GTC479. No MSP RNA was detected in GTC479 or GTC564 transfectants (data not shown). Prolonged exposure revealed residual levels of degraded MSP mRNA. The $^{35}$S labeled culture supernatants and the lysates were immunoprecipitated with a polyclonal antibody raised against MSP. Immunoprecipitation experiments showed that no expression from either the lysates or the supernatants of the GTC479 or GTC564 transfected cells (data not shown). These results showed that the native MSP-1 gene was not expressed in COS cells.

Native MSP-$1_{42}$ Gene is not Expressed in the Mammary Gland of Transgenic Mice The SalI-XhoI fragment of GTC479, which encoded the 15 amino acids of goat beta-casein signal peptide, the first 11 amino acids of goat beta-casein, and the native MSP-$1_{42}$ gene, was cloned into the XhoI site of the beta-casein expressed in vector BC350. This yielded plasmid BC574 (FIG. 7). A SalI-NotI fragment of BC574 was injected into the mouse embryo to generate transgenic mice. Fifteen lines of transgenic mice were established. Milk from the female founder mice was collected and subjected to Western analysis with polycolonal antibodies against MSP. None of the seven mice analyzed were found to express MSP-$1_{42}$ protein in their milk. To further determine if the mRNA of MSP-$1_{42}$ was expressed in the mammary gland, total RNA was extracted from day 11 lactating transgenic mice and analyzed by Northern blotting No MSP-$1_{42}$ mRNA was detected by any of the BC 574 lines analyzed. Therefore, the MSP-$1_{42}$ transgene was not expressed in the mammary gland of transgenic mice. Taken together, these experiments suggest that native parasitic MSP-$1_{42}$ gene could not be expressed in mammalian cells, and the block is as the level of mRNA abundance.

Expression of MSP in the Mammalian Cells

Figure 5:
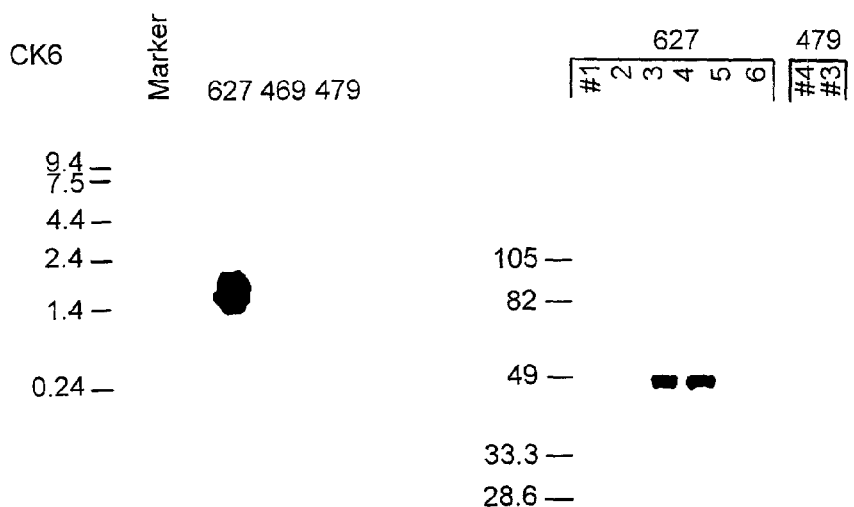
FIG. 5 panel A is a Northern analysis wherein construct GTC627 comprises the new MSP-$1_{42}$ gene modified in accordance with the invention, GTC479 is the construct comprising the native MSP-$1_{42}$ gene, and construct GTC469 is a negative control DNA.

Transient transfection experiments were performed to evaluate the expression of the modified MSP-$1_{42}$ gene of the invention in COS cells. GTC627 and GTC479 DNA were introduced into the COS-7 cells. Total RNA was isolated 48 hours post-transfection for Northern analysis. The immobilized RNA was probed with $^{32}$P labeled SalI-XhoI fragment of GTC627. A dramatic difference was observed between GTC479 and GTC627. White no MSP-1$_{42}$ mRNA was detected in the GTC479 transfected cells as shown previously, abundant MSP-1$_{42}$ mRNA was expressed by GTC627 (FIG. 5, Panel A). GTC 469 was used as a negative control and comprises the insert of GTC564 cloned into cloning vector PU19, a commercially available cloning vector. A metabolic labeling experiment with $^{35}$S methionine followed by immunoprecipitation with polyclonal antibody (provided by D. Kaslow NIAID, NIH) against MSP showed that MSP-1$_{42}$ protein was synthesized by the transfected COS cells (FIG. 5, Panel B). Furthermore, MSP-1$_{42}$ was detected in the transfected COS supernatant, indicating the MSP-1$_{42}$ protein was also secreted. Additionally, using Ni-NTA column, MSP-1$_{42}$ was affinity purified from the GTC627 transfected COS supernatant.

These results demonstrated that the modification of the parasitic MSP-1$_{42}$ gene lead to the expression of MSP mRNA in the COS cells. Consequently, the MSP-1$_{42}$ product was synthesized and secreted by mammalian cells.

Polyclonal antibodies used in this experiment may also be prepared by means well known in the art (*Antibodies: A Laboratory Manual,* Ed Harlow and David Lane, eds. Cold Spring Harbor Laboratory, publishers (1988)). Production of MSP serum antibodies is also described in Chang et al., *Infection and Immunity* (1996) 64:253–261 and Chang et al., (1992) *Proc Natl. Acad. Sci. USA* 86:6343–6347.

The results of this analysis indicate that the modified MSP-1$_{42}$ nucleic acid of the invention is expressed at a very high level compared to that of the natural protein which was not expressed at all. These results represent the first experimental evidence that reducing the AT % in a gene leads to expression of the MSP gene in heterologous systems and also the first evidence that removal of AUUUA mRNA instability motifs from the MSP coding region leads to the expression of MSP protein in COS cells. The results shown in FIG. 5, Panel A Northern (i.e. no RNA with native gene and reasonable levels with a modified DNA sequence in accordance with the invention), likely explains the increase in protein production.

The following examples describe the expression of MSP1-42 as a native non-fusion (and non-glycosylated) protein in the milk of transgenic mice.

Construction of MSP Transgene

To fuse MSP1-42 to the 15 amino acid β-casein signal peptide. a pair of oligos, MSP203 and MSP204 (MSP203: ggccgctcgacgccaccatgaaggtcctcataattgcc tgtctggtggctctggccattgcagccgtcactccctccgtcat, SEQ ID NO: 12; MSP204: cgatgacggagggagtgacggctg caatggccagagccaccagacaggcaattatgaggaccttcatggtggcgtcgagc, SEQ ID NO: 13). which encode the 15 amino acid-casein signal and the first 5 amino acid of the MSP1-42 ending at the Cla I site, was ligated with a Cla I-Xho I fragment of BC620 (FIG. 8) which encodes the rest of the MSP1-42 gene, into the Xho I site of the expression vector pCDNA3. A Xho I fragment of this plasmid (GTC669) was then cloned into the Xho I site of milk specific expression vector BC350 to generate B670 (FIG. 9)

Expression of MSP1-42 in the Milk of Transgenic Mice

Figure 10:
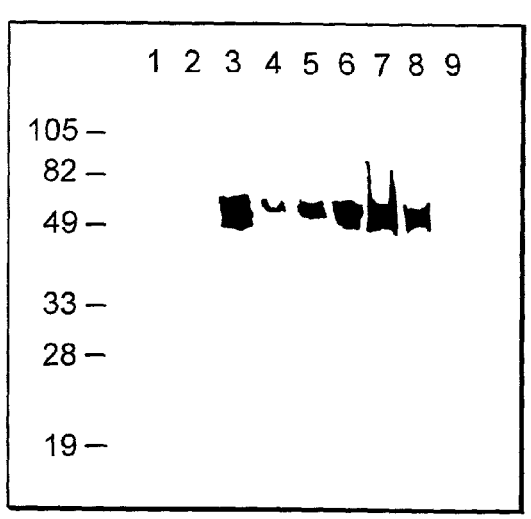
FIG. 10 is a representation of a Western blot of MSP transgenic milk.

A Sal I-Not I fragment was prepared from plasmid BC670 and microinjected into the mouse embryo to generate transgenic mice. Transgenic mice was identified by extracting mouse DNA from tail biopsy followed by PCR analysis using oligos GTC17 and MSP101 (sequences of oligos: GTC17, GATTGACAAGTAATACGCTGTTTCCTC, SEQ ID NO: 14. Oligo MSP101, GGATTCAATAGATACGG, SEQ ID NO: 15). Milk from the female founder transgenic mice was collected at day 7 and day 9 of lactation, and subjected to western analysis to determine the expression level of MSP1-42 using an polyclonal anti-MSP antibody and monoclonal anti MSP antibody 5.2 (Dr. David Kaslow. NIH). Results indicated that the level of MSP-1-42 expression in the milk of transgenic mice was at 1–2 mg/ml (FIG. 10).

Construction of MSP1-42 Glycosylation Sites Minus Mutants

Our analysis of the milk produced MSP revealed that the transgenic MSP protein was N-glycosylated. To eliminate the N-glycosylation sites in the MSP1-42 gene, Asn. (N) at positions 181 and 262 were substituted with Gln.(Q). The substitutions were introduced by designing DNA oligos that anneal to the corresponding, region of MSP1 and carry the AAC to CAG mutations. These oligos were then used as PCR primers to produce DNA fragments that encode the N to Q substitutions.

To introduce N262-Q mutation, a pair of oligos. MSPGYLYCO-3 (CAGGGAATGCTGCAGATCAGC, SEQ ID NO: 16) AND MSP42-2 (AATTCTCGAGTTAGTG GTGGTG-GTGGTGGTGATCGCAGAAAATACCATG, SEQ ID NO: 17; FIG. 11), were used to PCR amplify plasmid GTC627, which contains the synthetic MSP1-42 gene. The PCR product was cloned into pCR2.1 vector (Invitrogen). This (generated plasmid GTC716.

To introduce N181-Q mutation. oligos MSPGLYCO-1 (CTCCTTGTTCAGG AACTTGTAGGG, SEQ ID NO: 18) and MSPGLCO-2 (GTCCTGCAGTACACATATGAG, SEQ ID NO: 19; FIG. 4) were used to amplify plasmid GTC 627. The PCR product was cloned into pCR2.1. This generated plasmid GTC700.

Figure 12:
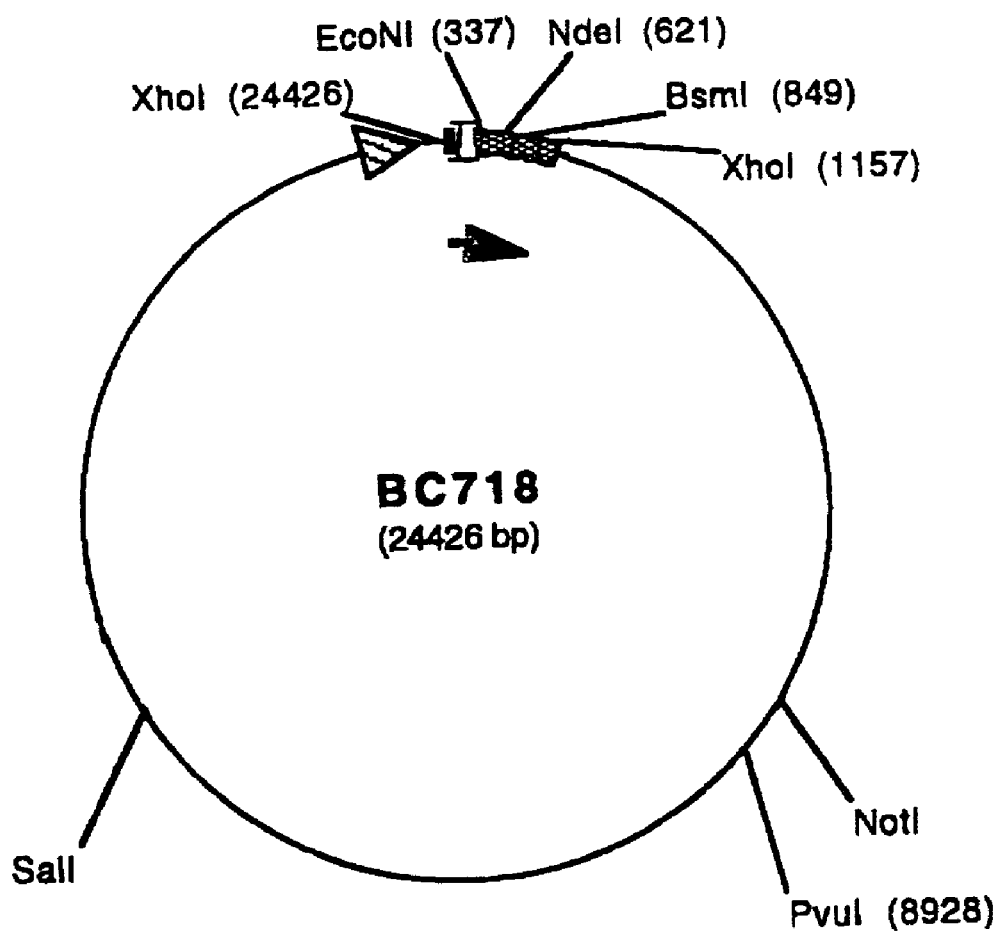
FIG. 12 is a schematic representation of the BC-718.

The MSP double glycosylation mutant was constructed by the following three steps: first, a Xho I-Bsm I fragment of BC670 and the Bsm I-Xho I fragment of GTC716 is ligated into the Xho I site of vector pCR2.1. This resulted a plasmid that contain the MSP-1-42 gene with N262-Q mutation. EcoN I-Nde I fragment of this plasmid was then replaced by the EcoN I-Nde I fragment from plasmid GTC716 to introduce the second mutation. N181-Q. A Xho I fragment of this plasmid was finally cloned into BC350 to generate BC718 (FIG. 12).

Transgenic Expression of Nonglycosylated MSP-1

BC718 has the following characteristics: it carries the MSP1-42 gene under the control of the β-casein promoter so it can be expressed in the mammary gland of the transgenic animal during lactation. Further, it encodes a 15 amino acid β-casein leader sequence fused directly to MSP1-42, so that the MSP1-42, without any additional amino acid at its N-terminal, can be secreted into the milk. Finally, because the N-Q substitutions. the MSP produced in the milk of the transgenic animal by this construct will not be N-glycosylated. Taken together, the transgenic MSP produced in the milk by BC718 is the same as the parasitic MSP.

Figure 13:
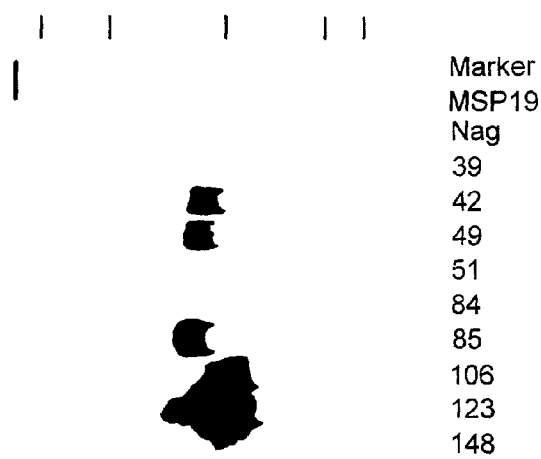
FIG. 13 is a representation of a Western blot of BC-718 expression in transgenic milk.

A SalI/XhoI fragment was prepared from plasmid BC718 and microinjected into mouse embryos to generate transgenic mice. Transgenic animals were identified as described previously. Milk from female founders was collected and analyzed by Western blotting with antibody 5.2. The results, shown in FIG. 13, indicate expression of nonglycosylated MSP1 at a concentration of 0.5 to 1 mg/ml.

SEQUENCE LISTING

<160> NUMBER OF SEQ ID NOS: 8

<210> SEQ ID NO 1
<211> LENGTH: 1065
<212> TYPE: DNA
<213> ORGANISM: preferably, a bacterium, virus, or parasite

<400> SEQUENCE: 1

```
gccgtcactc cctccgtcat cgataacatc ctgtccaaga tcgagaacga gtacgaggtg      60
ctgtacctga agccgctggc aggggtctac cggagcctga agaagcagct ggagaacaac     120
gtgatgacct tcaacgtgaa cgtgaaggat atcctgaaca gccggttcaa caagcgggag     180
aacttcaaga acgtgctgga gagcgatctg atcccctaca aggatctgac cagcagcaac     240
tacgtggtca aggatcccta caagttcctg aacaaggaga agagagataa gttcctgagc     300
agttacaact acatcaagga tagcattgat accgatatca acttcgccaa cgatgtcctg     360
ggatactaca agatcctgtc cgagaagtac aagagcgatc tggattcaat caagaagtac     420
atcaacgata agcagggaga gaacgagaag tacctgccct tcctgaacaa catcgagacc     480
ctgtacaaga ccgtcaacga taagattgat ctgttcgtga tccacctgga ggccaaggtc     540
ctgaactaca catatgagaa gagcaacgtg gaggtcaaga tcaaggagct gaattacctg     600
aagaccatcc aggataagct ggccgatttc aagaagaaca acaacttcgt cgggatcgcc     660
gatctgagca ccgattacaa ccacaacaac ctgctgacca gttcctgag caccggtatg     720 gtcttcgaaa acctggccaa gaccgtcctg agcaacctgc tggatgggaa cctgcagggg     780
atgctgaaca tcagccagca ccagtgtgtg aagaagcagt gtccccagaa cagcgggtgt     840
ttcagacacc tggatgagag agaggagtgt aagtgtctgc tgaactacaa gcaggaaggt     900
gataagtgtg tggaaaaccc caatcctact tgtaacgaga acaatggtgg atgtgatgcc     960
gatgccaagt gtaccgagga ggattcaggg agcaacggga agaagatcac ctgtgagtgt    1020
accaagcctg attcttatcc actgttcgat ggtatcttct gtagt                    1065
```

<210> SEQ ID NO 2
<211> LENGTH: 1088
<212> TYPE: DNA
<213> ORGANISM: preferably, a bacterium, virus, or parasite

<400> SEQUENCE: 2

```
gcagtaactc cttccgtaat tgataacata ctttctaaaa ttgaaaatga atatgaggtt      60
ttatatttaa aaccttttagc aggtgtttat agaagtttaa aaaaacaatt agaaaataac     120
gttatgacat ttaatgttaa tgttaaggat atttttaaatt cacgatttaa taacgtgaa     180 aatttcaaaa atgttttaga atcagattta attccatata aagatttaac atcaagtaat     240
tatgttgtca aagatcccata taaatttctt aataaagaaa aagagataa attcttaagc     300 agttataatt atattaagga ttcaatagat acggatataa attttgcaaa tgatgttctt     360
ggatattata aaatattatc cgaaaaatat aaatcagatt tagattcaat taaaaaatat     420
atcaacgaca acaaggtga aaatgagaaa taccttccct ttttaaacaa tattgagacc     480
ttatataaaa cagttaatga taaaattgat ttatttgtaa ttcatttaga agcaaaagtt     540
ctaaattata catatgagaa atcaaacgta gaagttaaaa taaagaact taattactta     600 aaaacaattc aagacaaatt ggcagatttt aaaaaaaata acaatttcgt tggaattgct     660
gatttatcaa cagattataa ccataataac ttattgacaa agttccttag tacaggtatg     720
```

```
gttttttgaaa atcttgctaa aaccgtttta tctaatttac ttgatggaaa cttgcaaggt      780
atgttaaaca tttcacaaca ccaatgcgta aaaaaacaat gtccacaaaa ttctggatgt      840
ttcagacatt tagatgaaag agaagaatgt aaatgtttat taaattacaa acaagaaggt      900
gataaatgtg ttgaaaatcc aaatcctact tgtaacgaaa ataatggtgg atgtgatgca      960
gatgccaaat gtaccgaaga agattcaggt agcaacggaa agaaaatcac atgtgaatgt     1020
actaaacctg attcttatcc acttttcgat ggtatttct gcagtcacca ccaccaccac     1080
cactaact                                                              1088

<210> SEQ ID NO 3
<211> LENGTH: 88
<212> TYPE: DNA
<213> ORGANISM: preferably, a bacterium, virus, or parasite

<400> SEQUENCE: 3
tcgacgagag ccatgaaggt cctcatcctt gcctgtctgg tggctctggc cattgcaaga       60
gagcaggaag aactcaatgt agtcggta                                          88

<210> SEQ ID NO 4
<211> LENGTH: 88
<212> TYPE: DNA
<213> ORGANISM: preferably, a bacterium, virus, or parasite

<400> SEQUENCE: 4
gatctaccga ctacattgag ttcttcctgc tctcttgcaa tggccagagc caccagacag       60
gcaaggatga ggaccttcat ggctctcg                                          88

<210> SEQ ID NO 5
<211> LENGTH: 60
<212> TYPE: DNA
<213> ORGANISM: preferably, a bacterium, virus, or parasite

<400> SEQUENCE: 5
taactcgagc gaaccatgaa ggtcctcatc cttgcctgtc tggtggctct ggccattgca       60

<210> SEQ ID NO 6
<211> LENGTH: 48
<212> TYPE: DNA
<213> ORGANISM: preferably, a bacterium, virus, or parasite

<400> SEQUENCE: 6
aattctcgag ttagtggtgg tggtggtggt gactgcagaa ataccatc                    48

<210> SEQ ID NO 7
<211> LENGTH: 31
<212> TYPE: DNA
<213> ORGANISM: preferably, a bacterium, virus, or parasite

<400> SEQUENCE: 7
aatagatctg cagtaactcc ttccgtaatt g                                      31

<210> SEQ ID NO 8
<211> LENGTH: 1142
<212> TYPE: DNA
<213> ORGANISM: preferably, a bacterium, virus, or parasite

<400> SEQUENCE: 8
atgaaggtcc tcataattgc ctgtctggtg gctctggcca ttgcagccgt cactccctcc       60
```

-continued

```
gtcatcgata acatcctgtc caagatcgag aacgagtacg aggtgctgta cctgaagccc    120
ctggcaggag tctacaggag cctgaagaag cagctggaga acaacgtgat gaccttcaac    180
gtgaacgtga aggatatcct gaacagcagg ttcaacaaga gggagaactt caagaacgtg    240
ctggagagcg atctgatccc ctacaaggat ctgaccagca gcaactacgt ggtcaaagat    300
ccctacaagt tcctgaacaa ggagaagaga gataagttcc tgagcagtta caattacatc    360
aaggatagca ttgacaccga tatcaacttc gccaacgatg tcctgggata ctacaagatc    420
ctgtccgaga agtacaagag cgatctggat agcatcaaga agtacatcaa cgataagcag    480
ggagagaacg agaagtacct gcccttcctg aacaacatcg agaccctgta caagaccgtc    540
aacgataaga ttgatctgtt cgtgatccac ctggaggcca aggtcctgca gtacacatat    600
gagaagagca acgtggaggt caagatcaag gagctgaatt acctgaagac catccaggat    660
aagctggccg atttcaagaa gaacaacaac ttcgtcggaa tcgccgatct gagcaccgat    720
tacaaccaca acaacctgct gaccaagttc ctgagcaccg aatggtctt cgaaaacctg    780
gccaagaccg tcctgagcaa cctgctggat ggaaacctgc agggaatgct gcagatcagc    840
cagcaccagt gtgtgaagaa gcagtgtccc cagaacagcg gatgcttcag acacctggat    900
gagagggagg agtgcaagtg cctgctgaac tacaagcagg aaggagataa gtgtgtggaa    960
aaccccaatc ctacttgtaa cgagaacaat ggaggatgcg atgccgatgc caagtgtacc   1020
gaggaggatt caggaagcaa cggaaagaag atcacctgcg agtgtaccaa gcctgattct   1080
tatccactgt tcgatggtat tttctgcagt caccaccacc accaccacta actcgaggat   1140
cc                                                                  1142
```

What is claimed is:

1. A non-human transgenic mammal whose genome comprises a modified SEQ ID NO: 2 encoding wild-type merozoite surface protein (MSP-1) operably linked to a mammary gland promoter,
wherein the modification reduces the AT content of SEQ ID NO: 2 by 50% or less by replacement of protozoan codons with codons preferred by mammalian cells,
wherein the replacement codons encode the same amino acid as the replaced codon, and
wherein the transgenic mammal expresses said modified SEQ ID NO: 2, thereby to produce MSP-1 in its milk.

2. The mammal of claim 1, wherein the promoter is a β-casein promoter.

3. The mammal of claim 1, wherein the modified SEQ ID NO: 2 encodes an MSP-1 comprising an amino acid sequence that lacks at least one glycosylation site.

4. The mammal of claim 3, wherein the modified SEQ ID NO: 2 encodes an MSP-1 comprising an amino acid sequence that lacks all glycosylation sites.

5. The mammal of claim 1, wherein the modified SEQ ID NO: 2 encodes an MSP-1 comprising an amino acid substitution at position 182.

6. The mammal of claim 1, wherein the modified SEQ ID NO: 2 encodes an MSP-1 comprising an amino acid substitution at position 263.

7. The mammal of claim 1, wherein the modified SEQ ID NO: 2 encodes an MSP-1 comprising amino acid substitutions at positions 181 and 263.

8. A method of producing a merozoite surface protein 1 (MSP-1) in the milk of a non-human transgenic mammal, comprising:

providing a non-human transgenic mammal whose genome comprises a modified SEQ ID NO: 2 encoding wild-type MSP-1 operably linked to a mammary gland promoter, wherein the modification reduces the AT content of SEQ ID NO: 2 by 50% or less by replacement of protozoan codons with codons preferred by mammalian cells, wherein the replacement codons encode the same amino acid as the replaced codon; and
allowing the transgenic mammal to express said modified SEQ ID NO: 2, thereby to produce MSP-1 in its milk.

9. The method of claim 8, wherein the promoter is a β-casein promoter.

10. The method of claim 8, wherein the modified SEQ ID NO: 2 encodes an MSP-1 comprising an amino acid sequence that lacks at least one glycosylation site.

11. The method of claim 10, wherein the modified SEQ ID NO: 2 encodes an MSP-1 comprising an amino acid sequence that lacks all glycosylation sites.

12. The method of claim 8, wherein the modified SEQ ID NO: 2 encodes an MSP-1 comprising an amino acid substitution at position 182.

13. The method of claim 8, wherein the modified SEQ ID NO: 2 encodes an MSP-1 comprising an amino acid substitution at position 263.

14. The method of claim 8, wherein the modified SEQ ID NO: 2 encodes an MSP-1 comprising amino acid substitutions at positions 181 and 263.

15. A non-human transgenic mammal whose genome comprises a modified SEQ ID NO: 2 encoding a wild-type MSP-1 operably linked to a mammary gland promoter, wherein the modification eliminates all the mRNA instability motifs in said SEQ ID NO: 2 by replacement of protozoan codons with codons preferred by mammalian cells, wherein the replacement codons encode the same amino acid as the replaced codon, and wherein the transgenic mammal expresses said modified SEQ ID NO: 2, to thereby produce MSP-1 in its milk.

16. The mammal of claim 15, wherein the promoter is a β-casein promoter.

17. The mammal of claim 15, wherein the modified SEQ ID NO: 2 encodes an MSP-1 comprising an amino acid sequence that lacks at least one glycosylation site.

18. The mammal of claim 17, wherein the modified SEQ ID NO: 2 encodes an MSP-1 comprising an amino acid sequence that lacks all glycosylation sites.

19. The mammal of claim 15, wherein the modified SEQ ID NO: 2 encodes an MSP-1 comprising an amino acid substitution at position 182.

20. The mammal of claim 15, wherein the modified SEQ ID NO: 2 encodes an MSP-1 comprising an amino acid substitution at position 263.

21. The mammal of claim 15, wherein the modified SEQ ID NO: 2 encodes an MSP-1 comprising amino acid substitutions at positions 182 and 263.

22. A method of producing a merozoite surface protein 1 (MSP-1) sequence in the milk of a non-human transgenic mammal, comprising:

providing a non-human transgenic mammal whose genome comprises a modified SEQ ID NO: 2 encoding a wild-type MSP-1 operably linked to a mammary gland promoter, wherein the modification eliminates all the mRNA instability motifs in said SEQ ID NO: 2 by replacement of protozoan codons with codons preferred by mammalian cells, and wherein the replacement codons encode the same amino acid as the replaced codon; and, allowing the transgenic mammal to express said modified SEQ ID NO: 2, to thereby produce MSP-1 in its milk.

23. The method of claim 22, wherein the promoter is a β-casein promoter.

24. The method of claim 22, wherein the modified SEQ ID NO: 2 encodes an MSP-1 comprising an amino acid sequence that lacks at least one glycosylation site.

25. The method of claim 24, wherein the modified SEQ ID NO: 2 encodes an MSP-1 comprising an amino acid sequence that lacks all glycosylation sites.

26. The method of claim 22, wherein the modified SEQ ID NO: 2 encodes an MSP-1 comprising an amino acid substitution at position 182.

27. The method of claim 22, wherein the modified SEQ ID NO: 2 encodes an MSP-1 comprising an amino acid substitution at position 263.

28. A transgenic non-human mammal whose genome comprises a modified SEQ ID NO: 2 encoding a wild-type MSP-1 operably linked to a mammary gland specific promoter, wherein the modification eliminates all the mRNA instability motifs of said SEQ ID NO: 2 by replacement of one or more protozoan codons with codons preferred by mammalian cells and the modification reduces the AT content of said SEQ ID NO: 2 by 50% or less by replacement of protozoan codons with codons preferred by mammalian cells, wherein the replacement codons encode the same amino acid as the replaced codon and wherein the transgenic mammal expresses said modified SEQ ID NO: 2, thereby to produce MSP-1 in its milk.

29. The mammal of claim 28, wherein the modified SEQ ID NO: 2 is expressed in milk at a level which is at least 25% more than the wild-type sequence is expressed under the same conditions.

30. The mammal of claim 28, wherein the modified SEQ ID NO: 2 is expressed in milk at a level which is at least 50% more than the wild-type nucleic acid sequence is expressed under the same conditions.

31. The mammal of claim 28, wherein the modified SEQ ID NO: 2 is expressed in milk at a level which is at least 100% more than the wild-type nucleic acid sequence is expressed under the same conditions.

32. The mammal of claim 28, wherein all protozoan codons are replaced with codons preferred by mammalian cells.

33. The mammal of claim 28, wherein the modified SEQ ID NO: 2 encodes an MSP-1 comprising an amino acid substitution at position 182.

34. The mammal of claim 28, wherein the modified SEQ ID NO: 2 encodes an MSP-1 comprising an amino acid substitution at position 263.

35. The mammal of claim 28, wherein the promoter is a β-casein promoter.

36. A method for producing a merozoite surface protein 1 (MSP-1) sequence in the milk of a non-human transgenic mammal, comprising:

providing a non-human transgenic mammal whose genome comprises a modified SEQ ID NO: 2 encoding a wild-type MSP-1 operably linked to a mammary gland promoter, wherein the nucleic acid has been modified by a) elimination of mRNA instability motifs by the replacement of protozoan codons in SEQ ID NO: 2 with codons preferred by mammalian cells; and b) reduction of AT content by 50% a or less by the replacement of one or more AT-containing protozoan codons of SEQ ID NO: 2 with codons preferred by mammalian cells, wherein the replacement codons encode the same amino acid as the replaced codon; and allowing the transgenic mammal to express said modified SEQ ID NO: 2, to thereby produce MSP-1 in its milk.

37. The method of claim 36, wherein the modified SEQ ID NO: 2 is expressed in milk at a level which is at least 25% more than the wild-type sequence is expressed under the same conditions.

38. The method of claim 36, wherein the modified SEQ ID NO: 2 is expressed in milk at a level which is at least 50% more than the wild-type nucleic acid sequence is expressed under the same conditions.

39. The method of claim 36, wherein the modified SEQ ID NO: 2 is expressed in milk at a level which is at least 100% more than the wild-type nucleic acid sequence is expressed under the same conditions.

40. The method of claim 36, wherein all protozoan codons are replaced with codons preferred by mammalian cells.

41. The method of claim 36, wherein the modified SEQ ID NO: 2 encodes an MSP-1 comprising an amino acid substitution at position 182.

42. The method of claim 36, wherein the modified SEQ ID NO: 2 encodes an MSP-1 comprising an amino acid substitution at position 263.

43. The method of claim 36, wherein the promoter is a beta casein promoter.

* * * * *